United States Patent [19]

Daren et al.

[11] Patent Number: 4,835,326

[45] Date of Patent: May 30, 1989

[54] STABILIZATION OF BROMOSTYRENES

[75] Inventors: Stephen L. J. Daren, Ness Ziona; David Vofsi, Haifa; Michael Peled, Beer Sheva, all of Israel

[73] Assignee: Yeda Research and Development Company Limited, Rehovot, Israel

[21] Appl. No.: 78,017

[22] Filed: Jul. 20, 1987

[30] Foreign Application Priority Data

Jul. 23, 1986 [IL] Israel ............................................ 79498

[51] Int. Cl.$^4$ .............................................. C07C 17/42
[52] U.S. Cl. .................................................... 570/105
[58] Field of Search ........................................... 570/105

[56] References Cited

U.S. PATENT DOCUMENTS

| | | | |
|---|---|---|---|
| 2,181,102 | 11/1939 | Stoesser et al. | 570/105 |
| 2,455,746 | 12/1948 | Erickson | 570/105 |
| 4,276,189 | 6/1981 | Jackisch | 570/105 |
| 4,338,474 | 7/1982 | Jackisch | 570/105 |
| 4,343,956 | 8/1982 | Jackisch | 570/105 |
| 4,375,006 | 2/1983 | Jackisch | 570/105 |

*Primary Examiner*—J. E. Evans
*Attorney, Agent, or Firm*—Browdy and Neimark

[57] ABSTRACT

The invention relates to the stabilization of monobromostyrene of dibromostyrene and of mixtures of these. The stabilization is effected by means of hydroxybenzene derivatives, where the benzene ring contains at least two substituents, one of these being a hydroxy group. The process is advantageously carried out by heating the styrene material with an excess of the inhibitor, distilling the monomer and adding an additional quantity of the inhibitor. The distilled monomer is preferably dried prior to the addition of the further quantity of inhibitor.

4 Claims, No Drawings

STABILIZATION OF BROMOSTYRENES

FIELD OF THE INVENTION

The present invention relates to a process for the stabilization of mono- and di-bromostyrene and of mixtures of these. The stabilization is effected by means of certain hydroxy-benzene derivatives, which can also be substituted by alkyl.

BACKGROUND OF THE INVENTION

Various processes have been suggested for the stabilization of bromostyrenes. Amongst these there may be mentioned U.S. Pat. Nos. 4,376,221, 4,276,189, 4,342,956, 4,338,474.

It is one of the drawbacks of the known processes that extremely high amounts of stabilizer (TBC, propyl gallate hindered amines etc.,) of the order of 800 ppm—are required to effect an acceptable degree of stabilization. Since the accepted practice in Industry is to effect polymerization without removing the inhibitor, amounts of 800 ppm introduce a level of impurities in the polymer that adversely affect the quality of the final products (colour, light stability, etc). The existing practice in the art calls for avoiding the use of stabilizers in excess of about 150 ppm in styrene monomer and the like.

SUMMARY OF THE INVENTION

The invention relates to a process for the stabilization of bromostyrene, dibromostyrene, or a mixture of these, which comprises heating same with an excess of a free radical polymerization inhibitor selected from:

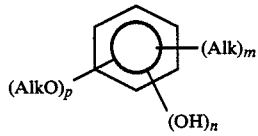

where n is 1, 2 or 3 and m is zero, 1 or 2, and p is zero or 1, where the benzene ring bears at least two subtituents, one being —OH, to an elevated temperature, distilling said monomer/s, and subsequently adding an additional quantity of a free-radical inhibitor, not exceeding about 150 ppm. A preferred embodiment relates to a process where the free radical inhibitor is tert-butyl catechol. We have found, that in bromostyrene monomers, prepared, for example, according to the process as described in the U.S. Pat. No. 4,292,453, there exists an impurity which interacts with tert-butyl catechol (TBC) and gradually causes its destruction. While the identity of said impurity or the nature of its reaction with TBC has not been elucidated, the mode of eliminating this impurity, and thereby removing the cause of destabilization of the BSMs (Bromostyrene Monomers) comprises the essence of the present invention.

Prior to the final distillation of the BSM or monomer mixture—an excess of TBC (Tertiary Butyl Catechol) of the order of about 1000 ppm is dissolved in the crude product and the mixture is heated to an elevated temperature for a certain time. The monomer (or mixture of mono and dibromostyrene) is then subjected to flash distillation under vacuum to produce the product. The procedure may be termed "sacrificial TBC treatment", since a certain amount of TBC is "sacrificed" in order to prevent premature polymerization of the final product.

After distillation, essentially no TBC remains in the distillate. An additional amount of about 150 ppm TBC is then added as stabilizer. The product is thereby stabilized to a degree far superior to that quoted in previous art (Ethyl Corporation patents), at a substantially reduced level of inhibitor.

It is advantageous to dry the distilled monomer over a conventional drying agent, such as silica gel. Examples of the use of such drying agent are given in the following examples, which are to be construed in a non-limitative manner.

EXAMPLE 1 (Comparative Example)

A 500 g sample of a crude mixture of mononbromo and dibromostyrene in a molar ratio of 70:30 prepared according to U.S. Pat. No. 4,292,453, was washed with a 1% ammonia solution, to remove trace acidity, followed by a final water wash. The mixture was then flash distilled at 2 mm Hg vacuum. The distilled monomer was then stabilized by the addition of 150 ppm tert. butyl catechol (TBC) and dried over 1 g of silica gel.

The storage stability of the monomer mixture was checked by keeping a 20 g sample in a stoppered glass vial in an oven at 75° C. and periodically testing an aliquot with four volumes of methanol. An absence of a cloud showed the absence of any polymer in the monomer. After 40 hours the first traces of polymer were detected.

EXAMPLE 2

A second sample of 500 g was prepared according to Example 1. Following the water wash and prior to the distillation, 800 ppm TBC were added to the crude monomer, and the mixture kept at 65° C. for 48 hours. At the end of this period, the TBC could no longer be detected by a colour test, after extracting a sample of the said mixture with aqueous NaOH. The mixture was then distilled under vacuum, dried over silica gel and stabilized by addition of 150 ppm TBC.

The thus treated monomer mixture was checked for storage stability at 75° C. as in Example 1. No trace of polymer was detected (by the cloud test with excess methanol) before expiration of 72 hours.

EXAMPLE 3

A run was carried out by the same procedure as in Example 2, but the crude monomer mixture was treated with 600 ppm TBC for 30 mins. at 90° C. prior to its final distillation. Addition of 150 ppm TBC to the distillate caused the stabilization of the product so that no polymer was detected for at least 87 hours at 75° C.

We claim:

1. A process for stabilizing brominated styrenes selected from the group consisting of bromostyrene, dibromostyrene, and mixtures thereof comprising:
   a first stage comprising heating said brominated styrene with an excess of a free radical polymerization inhibitor selected from the group consisting of:

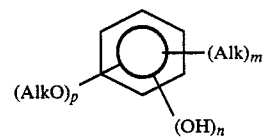

wherein n is 1, 2, or 3 and m is zero, 1, or 2, and p is zero or 1, wherein the benzene ring bears at least two substituents, at least one being —OH, to an elevated temperature, and distilling said brominated styrene, and a second stage comprising adding an additional quantity of said free-radical inhibitor, said quantity being not more than about 150 ppm.

2. A process according to claim 1, where the free radical inhibitor used in said first stage or in said second stage is tert-butyl catechol.

3. A process of stabilization according to claim 1, where the monomer is dried after distillation of the monomer.

4. The process according to claim 1 wherein there is used in the first stage from 600 to about 1000 ppm of the free radical polymerization inhibitor.

* * * * *